(12) United States Patent
Abdel-Aziz

(10) Patent No.: US 9,018,399 B1
(45) Date of Patent: Apr. 28, 2015

(54) METHOD FOR PREPARING CARBOXYLIC ACIDS

(71) Applicant: King Saud University, Riyadh (SA)

(72) Inventor: Hatem Abdel-Khader Abdel-Aziz, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 14/565,649

(22) Filed: Dec. 10, 2014

(30) Foreign Application Priority Data

Apr. 9, 2014 (EP) .................................. 14163967

(51) Int. Cl.
*C07D 333/38* (2006.01)
*C07D 333/24* (2006.01)
*C07D 333/40* (2006.01)
*C07C 51/305* (2006.01)
*C07D 307/85* (2006.01)
*C07B 41/08* (2006.01)

(52) U.S. Cl.
CPC ............ *C07D 333/40* (2013.01); *C07C 51/305* (2013.01); *C07D 307/85* (2013.01); *C07B 41/08* (2013.01)

(58) Field of Classification Search
CPC ........................... C07D 333/38; C07D 333/24
See application file for complete search history.

(56) References Cited

PUBLICATIONS

Y. Zhang et al.; Mild Conversion of β-Diketones and β-Ketoesters to Carboxylic Acids; Journal of Organic Chemistry, Feb. 13, 2006, pp. 4516-4520.
European Search Report for corresponding Application No. 14163967.4 dated Oct. 24, 2014.

*Primary Examiner* — Sun Jae Yoo
(74) *Attorney, Agent, or Firm* — Renner, Otto, Boisselle & Sklar, LLP

(57) ABSTRACT

The present invention discloses a method for the preparation of carboxylic acid comprising contacting β-ketosulfone of Formula (I) with nitrous acid.

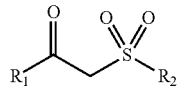

[Formula (I)]

14 Claims, No Drawings

METHOD FOR PREPARING CARBOXYLIC ACIDS

CROSS-REFERENCE TO RELATED APPLICATION AND PRIORITY CLAIM

The present application is related to and claims priority under 35 U.S.C. §119(a) to European Application No. 14163967.4, filed Apr. 9, 2014, entitled "Method for preparing carboxylic acids", the entirety of which is incorporated herein by reference.

TECHNICAL FIELD

The present invention relates to a method for preparing carboxylic acids.

BACKGROUND

Carboxylic acids are useful in several fields such as medical, industrial, nutritional and agricultural fields. The methods for preparation of carboxylic acids can be mainly classified into two types of reactions, oxidation and hydrolysis reactions.
(1) Oxidation Reactions:
(a) Oxidation of arene side-chains: Under strong oxidizing conditions such as hot acidic $KMnO_4$, arenes with benzylic-H are oxidized to the aromatic carboxylic acid. The oxidized side-chain substituent can be primary or secondary alkyl, while tertiary alkyl are not oxidized because they lack a benzylic-H. U.S. Pat. No. 3,282,992 describes the oxidation of ethylbenzene with aqueous ammonium dichromate at 225-275° C. yielded benzoic acid with minor amount of acetophenone and benzamide. Oxidation of arenes with side-chains higher than a methyl group can be considered as cleavage oxidation.
(b) Oxidation of primary alcohols: Primary alcohols can be oxidized to aldehydes or further to carboxylic acids. In aqueous media, the carboxylic acid is usually the major product when using reagents such as aqueous Cr (VI), chromic acid ($H_2CrO_4$), chromate salts ($Na_2CrO_4$), dichromate salts ($K_2Cr_2O_7$), permanganate $MnO_x$ and Jones' reagent ($CrO_3$/dil $H_2SO_4$/acetone). Anhydrous oxidants such as pyridinium chlorochromate (PCC) or pyridinium dichromate (PDC), which are used in dichloromethane, allow the oxidation to be stopped at the intermediate aldehyde. Secondary alcohols can be oxidized to ketones but no further, while tertiary alcohols cannot be oxidized since they have no carbinol C—H. For example, $CrO_3$-catalyzed oxidation of primary alcohols to carboxylic acids proceeds with 1-2 mol % of $CrO_3$ and 2.5 equivalents of $H_5IO_6$ in acetonitrile to give the corresponding carboxylic acids. Moreover, alcohols can be transferred into the corresponding carboxylic acids with aqueous 70% t-BuOOH in the presence of catalytic amounts of bismuth(III) oxide. By using Pd/C along with $NaBH_4$ in aqueous EtOH or MeOH and either $K_2CO_3$ or KOH at ambient temperature, alcohols can be oxidized to their carboxyl counterpart. Catalytic oxidation of alcohols can be realized by using o-iodoxybenzoic acid (IBX) in the presence of oxone as a co-oxidant. Pyridinium chlorochromate (PCC) catalyzed (2 mol %) oxidation of primary alcohols and aldehydes using 2.2 equivalents and 1.1 equivalents of $H_5IO_6$ leads to the synthesis of carboxylic acids. Selective aerobic oxidations in ionic liquids convert various primary alcohols into their corresponding acids or aldehydes in good yields. For examples, see M. Zhao et al., *Tetrahedron Lett.* 1998, 39, 5323-5326; P. Malik et al., *Synthesis* 2010, 3736-3740; M. Hunsen, *Synthesis* 2005, 2487-2490.
(c) Oxidation of aldehydes: Many of the stronger oxidizing agents, such as $KMnO_4$ and Tollens' reagent ($Ag_2O$; $Ag^+$/$NH_4OH$), can transform aldehydes into carboxylic acids. As an example, the oxidation of aldehydes to carboxylic acids can be realized utilizing oxone as an oxidant. In addition, carboxylic acids can be prepared from aldehydes using pyridinium chlorochromate (PCC) and $H_5IO_6$. Aromatic aldehydes can be oxidized to carboxylic acids using sodium perborate. Furthermore, permanganate can be applied as an oxidant in the transformation of aldehydes to carboxylic acids. For examples, see B. R. Travis et al., *Org. Lett.* 2003, 5, 1031-1034; A. McKillop et al., *Tetrahedron* 1989, 45, 3299-3306; J. Sedelmeyer et al., *Org. Lett.* 2010, 12, 3618-3621.
(d) Oxidative cleavage reactions: (i) Oxidative cleavage of ketones: Haloform reaction ($X_2$/NaOH, X=Cl, Br, I) has some synthetic utility in the oxidative demethylation of methyl ketones, if the other substituent on the carbonyl groups bears no enolizable α-protons. From an environmental point of view, the conversion of acetophenone to benzoic acid using sodium hypochlorite through haloform reaction is not suitable for industrial use due to the formation of chloroform as a side product. Homogeneous catalyst, such as 1,3-dinitrobenzene and nitric acid, can be used to oxidize acetophenone. However, nitric acid oxidation of acetophenone gives dibenzoylfurazan 2-oxide and benzoylformic acid in addition to benzoic acid. The liquid phase oxidation of acetophenone over rice husk silica vanadium catalyst leads to the products benzoic acid, 2-hydroxyacetophenone, phenol, acetic acid, and 3-hydroxyacetophenone. (S. Adam et al., *Chin. J. Catal.* 2012, 33, 518-522). Catalytic oxidation in vapour phase of acetophenone to benzoic acid over binary oxides $V_2O_5$—$MoO_3$ catalyst resulting in the formation of maleic anhydride, benzyl alcohol, benzaldehyde, benzoic acid, phthalic anhydride and trace amounts of toluene, xylene, and phenol. Although this method manages to achieve high selectivity towards benzoic acid, it needs high temperature and long contact times which are limitations. In addition, kinetics and mechanisms of the oxidation of methylaryl ketones by acid permanganate were studied. (ii) Oxidative cleavage of alkenes and alkynes: The oxidation of alkenes and alkynes by ozonolysis or acidic potassium permanganate ($KMnO_4$/$H_3O^+$) breaks the —CH═CH— bond, when a hydrogen atom is attached to each of the alkene carbons in the starting material. In case a hydrogen atom is attached to the carbonyl carbon in the product, the product is an aldehyde which can be rapidly transferred into a carboxylic acid group. If the alkene has no hydrogens attached, the product is a ketone which cannot be easily oxidized further. The alkyne is more highly oxidized than an alkene and the ozonolysis leads to the cleavage which involves the formation of a carboxylic acid groups. For examples, see V. R. Chumbahale et al., *Chem. Engi. Res. Design* 2005, 83, 75-80; M. P. Nath et al., *Aust. J. Chem.*, 1976, 29, 1939-1945. (iii) Oxidative cleavage of 1,2-diols: Organocatalytic one-pot oxidative cleavage of terminal 1,2-diols to one-carbon-unit-shorter carboxylic acids is catalyzed by 1-Me-AZADO in the presence of a catalytic amount of NaOCl and $NaClO_2$ under mild conditions. Aerobic photo-oxidative cleavage of 1,2-diols yields carboxylic acids using 2-chloroanthraquinone in the presence of photo-irradiation with a high-pressure mercury lamp. (iv) Oxidative cleavage of 1,3-di-carbonyls: Catalytic oxidative cleavage of 1,3-diketones enables the synthesis of the corresponding carboxylic acids, for example, by aerobic photo-oxidation with iodine under irradiation with a high-pressure mercury lamp or by conversion of β-ketoesters and β-diketones using CAN (cerium ammonium nitrate) in CH₃CN (Y. Zang et al., *J. Org. Chem.* 2006, 71, 4516-4520).

(2) Hydrolysis Reactions:

(a) Hydrolysis of nitriles and amides: Nitriles can be hydrolyzed to carboxylic acids without the isolation of amide intermediate. The carbon skeleton is extended by one carbon atom during this reaction sequence, in which the cyanide anion is a nucleophilic precursor of the carboxyl group. The hydrolysis may be either acid or base-catalyzed, but the latter gives a carboxylate salt as the initial product.

(b) Hydrolysis of acid chlorides, esters and anhydrides: N,N-diarylammonium pyrosulfate efficiently catalyzes the hydrolysis of esters under organic solvent-free conditions.

(3) Other Methods for Preparations of Carboxylic Acids:

(i) Benzilic acid rearrangement of 1,2-diketones: 1,2-Diketones undergo a rearrangement in the presence of strong base to yield α-hydroxycarboxylic acids. The best yields are obtained when the diketones do not have enolizable protons. (ii) Favorskii Reaction of cyclopropanones and α-halo ketones: The rearrangement of cyclopropanones, often obtained as intermediates from the base-catalyzed reaction of α-halo ketones, leads to the formation of carboxylic acids and their derivatives. (iii) Carboxylation of organometallics with CO₂: Organometallic intermediate compounds such as Grignard reagents react with carbon dioxide, as an electrophile, usually in Et₂O or THF followed by H₃O⁺ work-up. The initial product is a salt of the carboxylic acid, which must then be released by treatment with strong aqueous acid. (iv) Carboxylation of alcohols, esters, ethers or halides with CO: Alcohols, esters, ethers or halides can be converted to a carboxylic acid in the liquid phase with carbon monoxide at temperatures between 50-300° C. and at partial pressures of carbon monoxide 10-1,000 p.s.i.g., in the presence of a catalyst system containing rhodium and a halogen component as active constituents.

Nitrosation of active methylene compounds has been effected by nitrous acid, an inorganic nitrite and an acid, an alkyl nitrite and an inorganic acid or base, nitrosylchloride, nitrosylsulfuric acid, nitrogen trioxide and nitric oxide. However, none of these nitrosating agents is equally effective with all active methylene compounds. U.S. Pat. No. 2,749,358 describes a process for the preparation of oximes by reacting a nitric oxide and a compound containing an active methylene group by temperatures of 50 to 150° C. under pressure in the presence of a variable-valence-metal salt catalyst. Further, it is described that ease and degree of nitrosation depends primarily on the ability of the adjacent electron-attracting groups to promote nitrosation. Moreover, higher temperatures and pressure, longer reaction times and more active catalysts caused oxidation of the oximes formed to acids or oxidized tarry mixtures.

SUMMARY

It is an object of the present invention to provide a novel and efficient method for the preparation of carboxylic acid which overcomes the drawbacks of the prior art. In particular, a method shall be provided which allows the application of mild reaction conditions and enables the synthesis of various carboxylic acids with less or no formation of oxidative by-products.

This object is achieved by a method for preparing carboxylic acid comprising contacting β-ketosulfone of Formula (I) with nitrous acid,

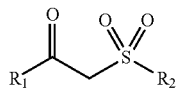

[Formula (I)]

wherein $R_1$ and $R_2$ represent each independently unsubstituted or substituted $C_1$-$C_{18}$ alkyl, which may be straight-chained or branched, unsubstituted or substituted $C_6$-$C_{20}$ aryl and unsubstituted or substituted $C_5$-$C_{20}$ heteroaryl, wherein one or more substitutent(s) of the substituted $C_1$-$C_{18}$ alkyl is each independently selected from halogen, unsubstituted or substituted amino, $C_1$-$C_4$ alkyl, alkoxy, haloalkoxy and unsubstituted or substituted aryl, and one or more substituent(s) of the substituted aryl and heteroaryl is each independently selected from halogen, alkyl, haloalkyl, alkoxy, haloalkoxy, alkylthio, alkylamino, aryl, heteroaryl, aryloxy, haloaryloxy, arylthio and arylamino.

The term "aryl" represents a carbocyclic moiety containing at least one benzenoid-type ring, i.e. may be monocyclic or polycyclic. Examples include but are not limited to phenyl, 1- or 2-naphthyl, anthryl, phenanthryl or biphenyl, which may be optionally substituted.

The term "heteroaryl" represents aromatic cyclic moiety, i.e. may be monocyclic or polycyclic, wherein said cyclic moiety is interrupted by at least one heteroatom selected from oxygen, sulfur or nitrogen. Examples of heteroaryls include but are not limited to pyridyl, quinolyl, isoquinolyl, benzothienyl, benzofuranyl, benzopyranyl, benzothiopyranyl, dihydrobenzopyranyl, dihydrobenzothiopyranyl, furanyl, pyrrolyl, or thienyl, which may be optionally substituted.

Moreover, the $C_6$-$C_{20}$ aryl and $C_5$-$C_{20}$ heteroaryl compounds may contain other atoms such as silicon and phosphorus.

The carboxylic acid is obtained through oxidative cleavage of the β-ketosulfone.

Furthermore, it is preferred that the nitrous acid ($HNO_2$) is formed in the presence of nitrite ($R_3$—$NO_2$), with $R_3$ being organic or inorganic.

It is preferred, that the inorganic nitrite is a metallic nitrite, in which $R_3$ is preferably Na, K or Ca, and the organic nitrite is a nitrite in which $R_3$ is $C_1$-$C_8$ alkyl, preferably is ethyl nitrite or isoamyl nitride.

In a preferred embodiment, the method is carried out under aqueous and/or acidic conditions.

More preferably, an acid is added to the reaction mixture, preferably an organic or mineral acid.

It is further preferred that the mineral acid is selected from the group consisting of phosphoric acid, nitric acid, sulfuric acid, hydrochloric acid, hydrobromic acid, hydroiodic acid and perchloric acid, preferably from phosphoric acid, nitric acid, sulfuric acid, hydrochloric acid and perchloric acid, and the organic acid is selected from acetic mono basic acids, preferably is selected from the group consisting of acetic acid, trifluoroacetic acid and difluoroacetic acid.

More preferably, a solvent is added, preferably water.

Even preferred, a co-solvent is added, preferably a water-miscible co-solvent, more preferably the co-solvent is selected from the group of $C_1$-$C_6$ alcohol, dimethylsulfoxide, dimethylformamide or mixtures thereof.

Preferably, the $C_1$-$C_6$ is a $C_1$-$C_3$ or $C_1$-$C_4$ alcohol, more preferably is selected from the group consisting of methanol, ethanol, n-propanol and/or isopropanol.

It is also preferred, that the reaction is stirred for 1 to 120 hours, preferably 12 to 60 hours, more preferably 46 to 50 hours.

Even preferred, the reaction temperature is in the range from 0 to 70° C., preferably 0 to 30° C.

In a preferred embodiment, water and/or solvent is removed under vacuum by azeotropic distillation, subsequent to the reaction.

It is preferred, that the method is for the preparation of aromatic carboxylic acids.

Surprisingly, it was found that the inventive method provides the possibility to prepare carboxylic acid through the oxidative cleavage of β-ketosulfones via nitrous acid under the application of mild reaction conditions and, additionally, enables the synthesis of various carboxylic acids with less or no formation of oxidative by-product. In the inventive method, the reaction may proceed through the formation of oximes as intermediates followed by the oxidative cleavage process of C—C bond. In general, normal ketones are not oxidized except on extreme hard conditions and give several products. The present invention allows even the preparation of respective carboxylic acids by the oxidative cleavage of β-ketosulfones via nitrous acid under mild conditions. The corresponding β-ketosulfones of Formula (I) can be prepared according to synthesis reported in prior art (for examples, see J. Xiang et al., *Bioorg. Med. Chem.* 2007, 15, 4396-4405; N. Suryakiran et al., *Tetrahedron Lett.* 2006, 47, 3853-3856; R. E. Swenson et al., *J. Org. Chem.* 2002, 67, 9182-9185; A. Kumar et al., *Tetrahedron Lett.* 2011, 52, 5368-5370; N. Samakkanad et al., *Synthesis* 2012, 44, 1693-1699; P. Sunitha et al., *Green Chem. Lett. Rev.* 2008, 1, 179-183).

Additional features and advantages of the present invention will become apparent in the following detailed description on the basis of the examples.

DETAILED DESCRIPTION

Examples

Example 1

4-Chlorobenzoic acid

To a stirred cold solution of 1-(4-chlorophenyl)-2-(phenylsulfonyl)ethanone (2.95 g, 10 mmol) in glacial acetic acid (30 ml), cold solution of sodium nitrite (0.7 g, 10 mmol) in water (10 ml) is added drop-wise with stirring at such a rate that the temperature remains in the range 0-5° C. over a period of 30 min, a light blue solution of nitrous acid is produced. The mixture is stirred for extra 48 h at 25° C. The solid that precipitated was collected, washed with water and dried, Recrystallization from EtOH afforded 4-chlorobenzoic acid in 65% yield; m.p. 238-240° C.; $^1$H NMR (DSMO-d$_6$) δ 7.57 (d, J=8.5 Hz, 2H, ArHs), 7.95 (d, J=8.5 Hz, 2H, ArHs), 13.20 (s, D$_2$O exchangeable, 1H, OH); $^{13}$C NMR (DSMO-d$_6$) δ 128.69, 129.72, 131.10, 137.70, 166.45; MS (EI) m/z 156 [M$^{+1}$], 157 [M$^+$+1], 158 [M$^+$+2]. 1-(4-Chlorophenyl)-2-tosylethanone afforded 4-chlorobenzoic acid in 72% yield.

Example 2

Biphenyl-4-carboxylic acid

Biphenyl-4-carboxylic acid was prepared from 1-(biphenyl-4-yl)-2-(phenylsulfonyl)ethanone following the same procedure described in example 1. Yield (62%); m.p. 225-227° C.; $^1$H NMR (DSMO-d$_6$) δ 7.43 (t, J=7.5 Hz, 1H, Ar), 7.51 (t, J=7.5 Hz, 2H, ArHs), 7.75 (d, J=7.5 Hz, 2H, ArHs), 7.79 (d, J=8.5 Hz, 2H, ArHs), 8.03 (d, J=8.5 Hz, 2H, ArHs), 13.00 (s, D$_2$O exchangeable, 1H, OH); $^{13}$C NMR (DSMO-d$_6$) δ 126.70, 126.91, 128.20, 129.04, 129.90, 139.07, 167.26; MS (EI) m/z 198 [M]$^1$.

Example 3

2-Naphthoic acid

2-Naphthoic acid was prepared from 1-(naphthalen-2-yl)-2-tosylethanone according to the procedure described in example 1 in 55% yield; m.p. 186-188° C.; $^1$H NMR (DSMO-d$_6$) δ 7.60-7.68 (m, 2H, ArHs), 7.98-8.03 (m, 3H, ArHs), 8.21 (d, J=8.0 Hz, 1H, ArH), 8.62 (s, 1H, ArH), 13.11 (s, D$_2$O exchangeable, 1H, OH); $^{13}$C NMR (DSMO-d$_6$) δ 125.25, 126.69, 127.60, 128.01, 128.14, 128.63, 129.20, 130.34, 132.14, 134.80, 167.56; MS (EI) m/z 172 [M]$^+$.

Example 4

Thiophene-2-carboxylic acid

Thiophene-2-carboxylic acid was prepared from 1-(thiophen-2-yl)-2-tosylethanone according to the procedure described in example 1 in 58% yield; m.p. 124-126° C.

Example 5

Benzofuran-2-carboxylic acid

Benzofuran-2-carboxylic acid was synthesized from 1-(benzofuran-2-yl)-2-(phenylsulfonyl)ethanone according to the procedure described in example 1 in 52% yield; m.p. 193-195° C.

The features disclosed in the foregoing description, claims and examples may, both separately or in any combination, be material for realizing the invention in diverse forms thereof.

The invention claimed is:

1. Method for preparing carboxylic acid comprising contacting β-ketosulfone of Formula (I) with nitrous acid,

[Formula (I)]

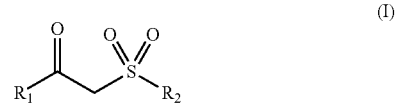

wherein $R_1$ and $R_2$ represent each independently unsubstituted or substituted $C_1$-$C_{18}$ alkyl, which may be straight-chained or branched, unsubstituted or substituted $C_6$-$C_{20}$ aryl or unsubstituted or substituted $C_5$-$C_{20}$ heteroaryl, wherein one or more substitutent(s) of the substituted $C_1$-$C_{18}$ alkyl is each independently selected from halogen, unsubstituted or substituted amino, $C_1$-$C_4$ alkyl, alkoxy, haloalkoxy or unsubstituted or substituted aryl, and one or more substituent(s) of the substituted $C_5$-$C_{20}$ aryl and $C_5$-$C_{20}$ heteroaryl is each independently selected from halogen, alkyl, haloalkyl, alkoxy, haloalkoxy, alkylthio, alkylamino, aryl, heteroaryl, aryloxy, haloaryloxy, arylthio or arylamino.

2. Method according to claim 1, wherein the nitrous acid is formed in the presence of nitrite ($R_3$—$NO_2$), with $R_3$ being organic or inorganic.

3. Method according to claim 2, wherein the inorganic nitrite is a metallic nitrite, and the organic nitrite is a nitrite in which $R_3$ is $C_1$-$C_8$ alkyl.

4. Method according to claim 1, wherein the method is carried out under aqueous and/or acidic conditions.

5. Method according to claim 1, wherein an acid is added to the reaction mixture.

6. Method according to claim 5, wherein the acid is a mineral acid selected from the group consisting of phosphoric acid, nitric acid, sulfuric acid, hydrochloric acid, hydrobromic acid, hydroiodic acid and perchloric acid, or the acid is an organic acid selected from acetic mono basic acids.

7. Method according to claim 1, wherein a solvent is added, preferably water.

8. Method according to claim 7, wherein a co-solvent is added.

9. Method according to claim 1, wherein the reaction is stirred for 1 to 120 hours.

10. Method according to claim 1, wherein the reaction temperature is in the range from 0 to 70° C.

11. Method according to claim 1, wherein, subsequent to the reaction water and/or solvent is removed.

12. Method according to claim 1, wherein the method is for the preparation of aromatic carboxylic acids.

13. Method according to claim 7, wherein the solvent is water.

14. Method according to claim 8, wherein the solvent is water and the co-solvent is water-miscible.

* * * * *